(12) United States Patent
Loper

(10) Patent No.: US 7,645,726 B2
(45) Date of Patent: Jan. 12, 2010

(54) DISPERSANT REACTION PRODUCT WITH ANTIOXIDANT CAPABILITY

(75) Inventor: John T. Loper, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 11/008,198

(22) Filed: Dec. 10, 2004

(65) Prior Publication Data

US 2006/0128571 A1    Jun. 15, 2006

(51) Int. Cl.
C10M 129/70 (2006.01)
C10M 133/00 (2006.01)

(52) U.S. Cl. .................................. 508/242; 508/463

(58) Field of Classification Search ............. 508/242, 508/463
See application file for complete search history.

(56) References Cited

U.S. PATENT DOCUMENTS

| | | | |
|---|---|---|---|
| 3,285,855 A | 11/1966 | Dexter | |
| 3,539,633 A | 11/1970 | Piasek | |
| 3,697,574 A | 10/1972 | Piasek | |
| 3,704,308 A | 11/1972 | Piasek | |
| 3,736,357 A | 5/1973 | Piasek | |
| 4,242,212 A * | 12/1980 | Hanson | 508/558 |
| 4,248,725 A * | 2/1981 | Crawford et al. | 508/229 |
| 4,334,085 A | 6/1982 | Basalay | |
| 5,071,919 A | 12/1991 | DeGonia | |
| 5,354,486 A * | 10/1994 | Evans | 508/501 |
| 5,399,178 A | 3/1995 | Cherpeck | |
| 5,439,607 A * | 8/1995 | Patil | 508/239 |
| 5,523,007 A | 6/1996 | Kristen | |
| 6,750,184 B2 | 6/2004 | Ribeaud et al. | |
| 6,784,142 B2 | 8/2004 | van Dam | |
| 2002/0006878 A1 | 1/2002 | Abraham et al. | |
| 2005/0113265 A1 | 5/2005 | Yagishita | |

FOREIGN PATENT DOCUMENTS

| | | |
|---|---|---|
| EP | 0 366 040 A1 | 5/1990 |
| JP | S62-241998 | 10/1987 |
| JP | S63-168492 | 7/1988 |
| JP | S63-273696 | 11/1988 |
| JP | H7-207287 | 8/1995 |
| JP | 11-20977 A | 3/1999 |
| SU | 265 080 | 1/1989 |
| WO | WO2004/003118 | 1/2004 |

OTHER PUBLICATIONS

Tochacek, J. & Sedlar, J.: "The influence of molecular weight on the efficiency of phenolic antioxidants as stabilisers for polypropylene—a short communication." Polymer Degradation and Stability, vol. 24, 1989, pp. 1-6, XP002374359 *compound IV*.
CS 265 080 B1 (Tochacek, J.; Sedlar, J.; Pac, J.) Sep. 12, 1989 *claims 1.2*.

* cited by examiner

*Primary Examiner*—Glenn Caldarola
*Assistant Examiner*—Jim Goloboy
(74) *Attorney, Agent, or Firm*—Fitch, Even, Tabin & Flannery; Kendrew H. Colton; Dennis Rainear

(57) ABSTRACT

A novel crankcase dispersant reaction product having fused therein an antioxidant moiety whereby the dispersant reaction product can function as an antioxidant while retaining at least two structural domains, one being a polar domain for association with sludge and a hydrocarbyl domain for oil solubility, so that the dispersant can function as a chemical agent to suspend sludge and prevent agglomeration of sludge precursors and soot so the latter can be readily removed from the system, such as by filtering, instead of being deleteriously deposited on internal engine components, as well as lubricant compositions incorporating such novel dispersant and, for instance, engines lubricated with such lubricant compositions.

16 Claims, No Drawings

DISPERSANT REACTION PRODUCT WITH ANTIOXIDANT CAPABILITY

FIELD OF THE INVENTION

The present invention pertains to novel dispersant reaction products and their method of preparation, lubricant compositions, methods of lubrication and products so lubricated. More particularly, the novel dispersant reaction product has both dispersant domains and antioxidant properties.

BACKGROUND OF THE INVENTION

Dispersants are important additives for lubricant compositions. Dispersants maintain impurities and deposits in a suspended state so that they can be removed from the system by filtration or other means rather than being deposited on internal engine components, gears, and transmissions.

Of the dispersants commonly used in lubricant applications, polymeric Mannich base additives, hydrocarbyl amine adducts, and hydrocarbyl succinic acid derivatives provide desirable properties for such applications. Mannich base dispersants are typically produced by reacting alkyl-substituted phenols with aldehydes and amines, such as is described in U.S. Pat. Nos. 3,539,633; 3,697,574; 3,704,308; 3,736,535; 3,736,357; 4,334,085; and 5,433,875.

Hydrocarbyl succinic acid based dispersants are derived by alkylating, for example, maleic anhydride, acid, ester or halide with an olefinic hydrocarbon to form an acylating agent as described in U.S. Pat. No. 5,071,919.

Despite the wide variety of dispersants available for lubricant applications, there remains a need for improved dispersants for gear and transmission lubricants and particularly for crankcase lubricant applications.

SUMMARY OF THE INVENTION

In one of the embodiments, a novel dispersant reaction product for use as a lubricant additive, a lubricant composition, a method for improving engine, gear or transmission performance is provided. In an aspect of the invention, a novel crankcase dispersant is obtainable as a dispersant reaction product by fusing (such as reacting) an antioxidant moiety to succinimide type or Mannich type dispersant. Fusing an antioxidant moiety to such dispersant can, in principle, localize the antioxidant to partially oxidized hydrocarbon sludge that can form in a crankcase. An illustrative novel dispersant having antioxidant properties is obtainable by reacting a succinimide type and/or Mannich type dispersant with a phenolic-substituted ester or acid.

In an embodiment, there is provided a novel dispersant reaction product obtainable by reacting at least one succininide and/or Mannich based dispersant with an R-(3,5-dihydrocarbyl, 4-hydroxy phenyl) 2-$R_3$-propionate, wherein the 3-5-di-hydrocarbyl moieties can be independently a $C_1$-$C_6$ alkyl, branched or linear, including methyl, ethyl, i-propyl and t-butyl as examples, $R_3$ can be hydrogen or an alkyl moiety, such as lower alkyl of which methyl or ethyl are examples, and R can represent a linear or branched alkoxy group, such as one having 1 to 6 carbon atoms as an example. At least one of the hydrocarbyl groups at the 3 and 5 positions is preferably branched, and can be, for instance, a t-alkyl group, such as a t-butyl group as an example.

In yet another embodiment, a method of reducing engine deposits in an internal combustion engine of a vehicle is provided. The method includes using, as a crankcase lubricating oil for the internal combustion engine, a lubricant composition containing a lubricant and a lubricant additive. The lubricant additive includes a reaction product of (1) a dispersant including a member selected from the group of succinimide type dispersants, hydrocarbyl-substituted amines, and Mannich type dispersants and (2) a phenolic-substituted ester or acid as described herein.

Advantageously, various aspects of the inventions described herein provide improved dispersants for lubricant compositions, lubricant compositions containing the improved dispersants, and methods for improving engine, gear or transmission performance using the improved dispersants. Dispersants in the lubricating oil suspend thermal decomposition and oxidation products, such as soot and sludge, and reduce or retard the formation of deposits on lubricated surfaces. Dispersant reaction products provided according to the following disclosure can exhibit an increased polar functionality for association with sludge while remaining substantially dissolved in an oleaginous fluid, all the while being capable of exhibiting antioxidant properties or functioning as an antioxidant.

The dispersant reaction products described herein are particularly suitable for being added to crankcase lubricants for diesel and gasoline engines, as a dispersant for automatic or manual transmission fluids, as an additive for continuously variable gear oils, and as a component of hydraulic oils. Other features and advantages of the dispersant reaction products will be evident by reference to the following detailed description which is intended to exemplify aspects of the preferred embodiments without intending to limit the embodiments described herein.

DETAILED DESCRIPTION OF THE INVENTION

A novel dispersant reaction product according to the present invention can include an antioxidant moiety from:

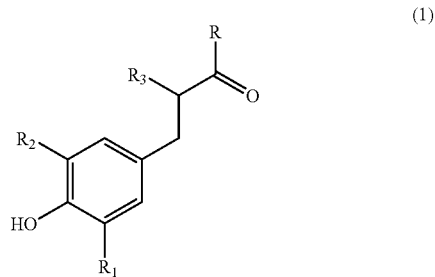

(1)

wherein R represents an alkoxy group or —OH, $R_1$ and $R_2$ independently represent a branched or linear aliphatic hydrocarboxyl group, such as an alkyl group containing 1 to 6 carbon atoms, and $R_3$ represents alkyl or a hydrogen atom (H). When R represents alkoxy, a suitable, exemplary, R moiety is —$OC_{1-6}$, including a methoxy group as an example. R can be a —$OC_{1-4}$ moiety. $R_1$ and $R_2$ can be the same or different and can be, for instance, methyl, ethyl, n-propyl, i-propyl, n-butyl, s-butyl, t-butyl, n-hexyl and the like. $R_1$ and $R_2$ can represent the same or different branched alkyl groups. By preference, at least one of $R_1$ and $R_2$ is a t-alkyl group, such as t-butyl, and preferably both are t-alkyl. When $R_3$ is alkyl, it can include a lower alkyl group, such as methyl or ethyl as examples.

An antioxidant reactable with a succinimide type dispersant or Mannich type dispersant to obtain a reaction product (dispersant) of the present invention is also exemplified by the phenolic-substituted compound represented by the formula:

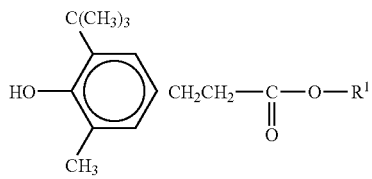

This compound is further described in JP-A-11-20977 (1999). Other suitable sources for a reactable antioxidant for introducing an antioxidant moiety include the phenolic ester antioxidants described in US 2002/0006878A (Jan. 17, 2002), such as:

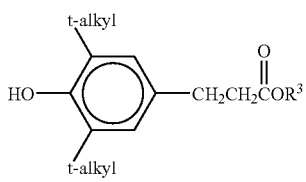

wherein $R_3$ is an alkyl containing 2-6 carbon atoms, such as n-butyl; and, in principle, the phenolic esters described in U.S. Pat. No. 5,523,007:

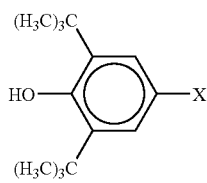

where X can be —$CH_2$—$CH_2$—C(=O)—OR and R is a straight or branched alkyl radical —$C_nH_{2n+1}$ with n=1 to 22; and, in principle, the compounds as described in U.S. Pat. No. 3,285,855:

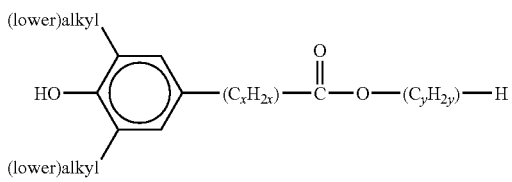

wherein X is an integer of 0 to 6, y is a value of from 6 to 30; and, in principle, the phenolic ester antioxidants described in U.S. Pat. Nos. 6,750,184B2 and 6,784,142B2, among others, the complete disclosures of which are incorporated herein by reference.

In principle, in an embodiment of the present invention, a novel dispersant reaction product is obtainable as illustrated in the hereinbelow reaction scheme:

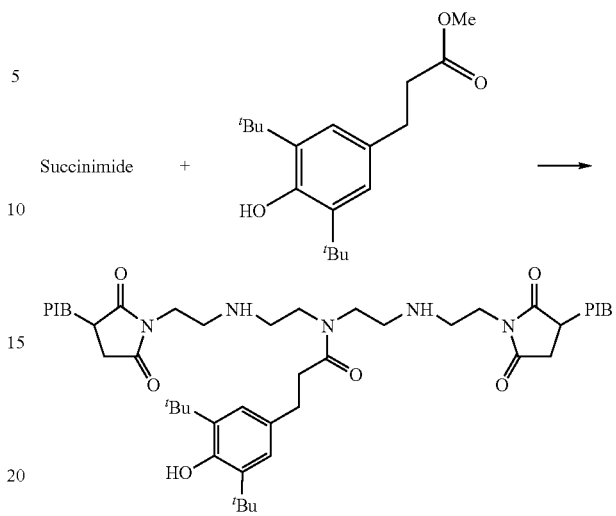

As illustrated, R is —$OCH_3$, $R_3$ is hydrogen, $R_1$ and $R_2$ are t-butyl ($^tBu$), and PIB represents a moiety based on a polyisobutylene as an exemplary hydrocarbyl-substituent. It should be understood that any antioxidant species represented by formula (1), such as when $R_3$ is methyl as an example, and/or another of the suitable, reactable antioxidant species as described herein can be used in the reaction.

One or more dispersant reaction products according to the invention can be used as additive(s) in a dispersant formulation (such as an additive package) or in a lubricant composition. As will be appreciated, the dispersant reaction product is prepared for subsequent use in an additive package, lubricant and the like as distinguished from any degradation or other products that might be generated in situ when using a conventional lubricant composition to lubricate an engine.

The ratio of the phenolic substituted ester or acid to the reactable dispersant, which may be a succinimide or Mannich type dispersant, is dependent upon the number of titratable nitrogen atoms present within the reactable dispersant. The molar equivalents of phenolic-substituted ester can range from 0.1 n to n, wherein n represents the number of basic nitrogen atoms present within the reactable dispersant molecule.

Succinimide type dispersants suitable for reacting with a phenolic-substituted ester or acid include those that may be prepared, for example, by reacting hydrocarbyl-substituted succinic acid(s) or anhydride(s) with an amine.

One suitable succinimide type dispersant is the reaction product of a long chain hydrocarbyl-substituted succinic acylating agent and a polymine as described in U.S. Pat. No. 6,800,596. The long chain hydrocarbyl group is derived for example from ($C_2$-$C_{10}$) polymer, e.g., a polymer of a ($C_2$-$C_5$) monoolefin(s), wherein the polymer can have a number average molecular weight (Mn) of about 500 to about 10,000. Exemplary olefin polymers for reaction with the unsaturated dicarboxylic acid anhydride or ester are polymers comprising a major molar amount of ($C_2$-$C_{10}$) polymer, e.g., a polymer of a ($C_2$-$C_5$) monoolefin(s). Such olefins include ethylene, propylene, butylene, isobutylene, pentene, 1-octene, styrene, etc. The polymers can be homopolymers such as polyiosbutylene, as well as copolymers of two or more of such olefins such as copolymers of: ethylene and propylene, butylene and isobutylene, propylene and isobutylene, etc. Other copolymers include those in which a minor molar amount of the copolymers e.g., 1 to 10 mole % is a ($C_4$-$C_{10}$) non-conjugated diolefin, e.g., a copolymer of isobutylene and butadiene; or a copolymer of ethylene, propylene and 1,4-hexadiene; etc. The bis-alkenyl succinimide, in one example, has a succinic anhydride to polyisobutylene ratio ranging from about 0.9 to about 4.0, and has an anhydride to amine ratio ranging from about 1:1 to about 3:1. In some cases, the olefin polymer may be completely saturated, for example an ethylene-propylene copolymer made by a Ziegler-Natta synthesis using hydrogen as a moderator to control molecular weight. In one example, the alpha- and beta-unsaturated dicarboxylic acid anhydride is reacted with the saturated ethylene-propylene copolymer utilizing a radical initiator. The long chain hydrocarbyl-substituted succinic acylating agent, e.g., acid or anhydride, includes a long chain hydrocarbon, generally a polyolefin, substituted typically with an average of at least about 0.8 per mole of polyolefin, of an alpha- or beta-unsaturated ($C_4$-$C_{10}$) dicarboxylic acid, anhydride or ester thereof, such as fumaric acid, itaconic acid, maleic acid, maleic anhydride, chloromaleic acid, dimethylfumarte, chloromaleic anhydride, acrylic acid methacrylic acid, crotonic acid, cinnamic acid, and mixtures thereof.

Preferred amines are selected from polyamines and hydroxyamines. Examples of polyamines that may be used include, but are not limited to, diethylene triamine (DETA), triethylene tetramine (TETA), tetraethylene pentamine (TEPA), and higher homologues such as pentaethylamine hexamine (PEHA), E-100 polyamine (Huntsman Chemical), and HP-X polyamine (Dow Chemical), and the like.

A suitable heavy polyamine is a mixture of polyalkylenepolyamines comprising small amounts of lower polyamine oligomers such as TEPA and PEHA (pentaethylene hexamine) but primarily oligomers with 6 or more nitrogen atoms, 2 or more primary amines per molecule, and more extensive branching than conventional polyamine mixtures. A heavy polyamine preferably includes polyamine oligomers containing 7 or more nitrogens per molecule and with 2 or more primary amines per molecule. The heavy polyamine comprises more than 28 wt. % (e.g. >32 wt. %) total nitrogen and an equivalent weight of primary amine groups of 120-160 grams per equivalent.

Commercially available, suitable polyamines are commonly known as PAM, and contain a mixture of ethylene amines where TEPA and pentaethylene hexamine (PEHA) are the major part of the polyamine, usually less than about 80%. PAM is commercially available from suppliers such as Huntsman Chemical under the trade name E-100 or from the Dow Chemical Company under the trade name HPA-X. The commercially available PAM mixture typically consists of less than 1.0 wt. % low molecular weight amine, 10-15 wt. % TEPA, 40-50 wt. % PEHA and the balance hexaethyleneheptamine (HEHA) and higher oligomers. Typically PAM has 8.7-8.9 milliequivalents of primary amine per gram (an equivalent weight of 115 to 112 grams per equivalent of primary amine) and a total nitrogen content of about 33-34 wt. %.

Heavier cuts of PAM oligomers with practically no TEPA and only very small amounts of PEHA but containing primarily oligomers with more than 6 nitrogens and more extensive branching, produce dispersants with improved dispersancy. An example of one of these heavy polyamine compositions is commercially available from the Dow Chemical Company under the trade name of Polyamine HA-2.

HA-2 is prepared by distilling out the lower boiling polyethylene amine oligomers (light ends) including TEPA. The TEPA content is less than 1 wt. %. Only a small amount of PEHA, less than 25 wt. %, usually 5-15 wt. %, remains in the mixture. The balance is higher nitrogen content oligomers usually with a greater degree of branching. The heavy polyamine as used herein is preferably devoid of oxygen atoms.

Typical analysis of HA-2 gives primary nitrogen values of about 7.8 milliequivalents (meq) (e.g. 7.7-7.8) of primary amine per gram of polyamine. This calculates to be about an equivalent weight (EW) of 128 grams per equivalent (g/eq). The total nitrogen content is about 32.0-33.0 wt. %. Commercial PAM analyzes for 8.7-8.9 meq of primary amine per gram of PAM and a nitrogen content of about 33 to about 34 wt. %.

Succinimide type dispersants can be derived from 350 to 5,000 Mn PIB and can have a succinic anhydride to PIB (polyisobutylene) ratio ranging from 0.8 to 4.0. In one embodiment, the mole ratio of amine to hydrocarbyl-succinic acid or anhydride can range from about 1:1 to about 1:9. In another embodiment, the mole ratio can be from about 1:1 to about 1:3.

A commercially available succinimide type dispersant that can be utilized in preparing a reaction product of the present invention is a HiTEC® 1932 brand dispersant, which is a commercially available bis-succinimide dispersant that is derived from a 2100 Mn PIBSA and a polyamine having a SA/PIB ratio of greater than about 1.1, which is available from Afton Chemical Corporation. "PIBSA" is defined as polyisobutylene succinic acid or anhydride. The "SA/PIB" ratio is the number of moles of succinic acid or anhydride relative to the number of moles of PIB in the PIBSA adduct.

The Mannich base dispersants useful in preparing a reaction product of the present invention are themselves preferably a reaction product of an alkyl phenol, typically having a long chain alkyl substituent on the ring, with one or more aliphatic aldehydes containing from 1 to about 7 carbon atoms (especially formaldehyde and derivatives thereof), and polyamines (especially polyalkylene polyamines). Examples of Mannich condensation products, and methods for their production are described in U.S. Pat. Nos. 2,459,112; 2,962,442; 2,984,550; 3,036,003; 3,166,516; 3,236,770; 3,368,972; 3,413,347; 3,442,808; 3,448,047; 3,454,497; 3,459,661; 3,493,520; 3,539,633; 3,558,743; 3,586,629; 3,591,598; 3,600,372; 3,634,515; 3,649,229; 3,697,574; 3,703,536; 3,704,308; 3,725,277; 3,725,480; 3,726,882; 3,736,357; 3,751,365; 3,756,953; 3,793,202; 3,798,165; 3,798,247; 3,803,039; 3,872,019; 3,904,595; 3,957,746; 3,980,569; 3,985,802; 4,006,089; 4,011,380; 4,025,451; 4,058,468; 4,083,699; 4,090,854; 4,354,950; and 4,485,023.

The preferred hydrocarbon sources, for preparation of the Mannich polyamine dispersants are those derived from substantially saturated petroleum fractions and olefin polymers, preferably polymers of mono-olefins having from 2 to about 6 carbon atoms. The hydrocarbon source generally contains at least about 40 and preferably at least about 50 carbon atoms to provide substantial oil solubility to the dispersant. The olefin polymers having a GPC number average molecular weight between about 500 and 5,000 are preferred for reasons of easy reactivity and low cost. However, polymers of higher molecular weight can also be used.

The preferred reactable Mannich base dispersants are Mannich base ashless dispersants formed by condensing about one molar proportion of long chain hydrocarbon-substituted phenol with from about 1 to 2.5 moles of formaldehyde and from about 0.5 to 2 moles of polyalkylene polyamine.

A reaction product according to an aspect of the present invention can be formulated to obtain a lubricant concentrate or a lubricant composition. The reaction product, e.g., modified dispersant as described herein, is preferably provided as a concentrate in a base oil. Base oils suitable for use in formulating lubricating oil compositions may be selected from any of the synthetic or natural oils or mixtures thereof.

The base oil used which may be used to make lubricant compositions as described herein may be selected from any of the base oils in Groups I-V as specified in the American Petroleum Institute (API) Base Oil Interchangeability Guidelines. Such base oil groups are as follows:

| Base Oil Group[1] | Sulfur (wt. %) | | Saturates (wt. %) | Viscosity Index |
|---|---|---|---|---|
| Group I | >0.03 | and/or | <90 | 80 to 120 |
| Group II | ≦0.03 | And | ≧90 | 80 to 120 |
| Group II | ≦0.03 | And | ≧90 | ≧120 |
| Group IV | all polyalphaolefins (PAOs) | | | |
| Group V | all others not included in Groups I-IV | | | |

[1]Groups I-III are mineral oil base stocks.

Another component of an additive or additive concentrate according to the embodiments described herein is a multi-functional viscosity index improver such as known in the art and commercially available. These products and the processes for making them are taught in, for example, U.S. Pat. Nos. 4,732,942; 4,863,623; 5,075,383; 5,112,508; 5,238,588; and 6,107,257, each of which is incorporated herein by reference.

The multi-function viscosity index improver is preferably a nitrogen-containing viscosity index improver. Multi-functional viscosity index improvers include the reaction product of a nitrogen or an oxygen and nitrogen containing ethylenically unsaturated, aliphatic or aromatic monomer grafted on to an olefin copolymer. Suitable nitrogen or oxygen and nitrogen containing ethylenically unsaturated monomers include N-vinyl imidazole, 1-vinyl-2-pyrrolidinone, N-allyl imidazole, allyl amines, 1-vinyl pyrrolidone, 2-vinyl pyridine, 4-vinyl pyridine, N-methyl-N-vinyl acetamide, diallyl formamide, N-methyl-N-allyl formamide, N-ethyl-N-allyl formamide, N-cyclohexyl-N-allyl formamide, 4-methyl-5-vinyl thiazole, N-allyl di-iso-octyl phenothiazine, 2-methyl-1-vinylimidazole, 3-methyl-1-vinylpyrazole, N-vinyl purine, N-vinyl piperazines, N-vinyl succinimide, vinylpiperidines, vinylmorpholines, N-arylphenylenediamines, and mixtures thereof.

The multi-functional copolymers described above, as well as processes for preparing them, are described in U.S. Pat. Nos. 4,092,255; 4,170,561; 4,146,489; 4,715,975; 4,769,043; 4,810,754; 5,294,354; 5,523,008; 5,663,126; and 5,814,586; and 6,187,721, each of which is incorporated herein by reference.

Non-dispersant viscosity index improvers may be used in the alternative or in combination with the foregoing nitrogen containing viscosity index improvers. Such non-dispersant viscosity index improvers include, but are not limited to, olefin copolymers, polyalkylmethacrylates, and styrene-maleic esters. Of these, polyalkylmethacrylates are particularly preferred. The viscosity index improver may be supplied in the form of a solution in an inert solvent, typically a mineral oil solvent, which usually is a severely refined mineral oil.

Suitable materials for use a viscosity index improvers include styrene-maleic esters such as LUBRIZOL® 3702, LUBRIZOL® 3706 and LUBRIZOL® 3715 available from The Lubrizol Corporation; polyalkylmethacrylates such as those available from ROHM GmbH (Darmstadt, Germany) under the trade designations: VISCOPLEX®5543, VISCOPLEX® 5548, VISCOPLEX® 5549, VISCOPLEX® 5550, VISCOPLEX® 5551 and VISCOPLEX® 5151, from Rohm & Haas Company (Philadelphia, Pa.) under the trade designations ACRYLOID® 1277, ACRYLOID® 1265 and ACRYLOID® 1269, and from Ethyl Corporation (Richmond, Va.) under the trade designation HiTEC® 5710 VII; and olefin copolymer viscosity index improvers known by brand names such as HiTEC® 5747 VII, HiTEC® 5751 VII, HiTEC® 5770 VII and HiTEC® 5772 VII available from Ethyl Corporation and SHELLVIS® 200 available from Shell Chemical Company. Mixtures of the foregoing products can also be used as well as dispersant and dispersant-antioxidant viscosity index improves.

Additives used in formulating the compositions described herein may be blended into the base oil individually or in various sub-combinations. However, it is preferable to blend all of the components concurrently using an additive concentrate (i.e., additives plus a diluent, such as a hydrocarbon solvent). The use of an additive concentrate takes advantage of the mutual compatibility afforded by the combination of ingredients when in the form of an additive concentrate. Also, the use of a concentrate reduces blending time and lessens the possibility of blending errors.

A formulated additive package can comprise the novel dispersant reaction product according to the invention, optionally at least one other additive suitable for an oil-based lubricating composition, and a minor amount of an oil. A formulated additive package can contain 10 wt. % to 80 wt. % of the present novel dispersant reaction product, as an example.

Another aspect of the present invention is directed to a method of reducing deposits in an internal combustion engine. In this embodiment, the method includes using as the crankcase lubricating oil for the internal combustion engine a lubricating oil to which is added (such as by blending) the dispersant reaction product as described herein. The dispersant reaction product is present in an amount sufficient to reduce deposits in an internal combustion engine operated using the crankcase lubricating oil, as compared to deposits in an engine operated in the same manner and using the same crankcase lubricating oil, except that the oil is devoid of the dispersant. Accordingly, for reducing deposits, the modified dispersant is preferably present in the lubricating oil in an amount of from 1 to 10 weight percent based on the total weight of the oil. In other embodiments, the lubricant compositions described herein may be used or formulated as gear oils, hydraulic oils, automatic or manual transmission fluids, and the like.

A succinimide type dispersant is heated to at an elevated temperature, such as about 70° C. and about 200° C. as an example, under an inert atmosphere (nitrogen or the like) in a suitable reaction vessel. A hindered phenolic ester is added. The reaction mixture is stirred at a sufficient temperature for a sufficient time so the reaction can proceed to completion. A sufficient temperature can range from about 70° C. to about 200° C., and more particularly, from about 100° C. to about 160° C., as examples A sufficient time can be about 2 to 6 hours, and more particularly from about 2 to about 4 hours, as examples for batch production. The formation of the amide can be followed using FTIR. The reaction product obtainable is diluted with process oil and is filtered.

The following Example(s) are given for the purpose of exemplifying aspects of the embodiments and is not intended to limit the embodiments or claims in any way.

EXAMPLE 1

To a 1 liter resin kettle equipped with an overhead stirrer, a Dean-Stark trap and a thermocouple was charged 993 g of an alkenyl succinimide dispersant (derived from 1300 Mn PIB) and 73 g of methyl 3-((3,5-di-t-butyl)-4-hydroxyl phenyl) propionate. The reaction mixture obtained was heated with stirring under nitrogen atmosphere at 160° C. for 4 hours. The reaction mixture was diluted with 43 g of process oil to afford 1074 g of product.

EXAMPLE 2

To a 1 liter resin kettle equipped with an overhead stirrer, a Dean-Stark trap and a thermocouple was charged 518.5 g of an alkenyl succinimide (HiTEC 1932® brand dispersant from Afton Chemical Corporation) and 20.5 g of methyl 3-((3,5-di-t-butyl)-4-hydroxyl phenyl) propionate. The reaction mixture obtained was heated with stirring under nitrogen atmosphere at 160 C for 4 hours. The reaction mixture was diluted with 25.2 g of process oil to afford the desired product.

EXAMPLE 3

To a 2 liter resin kettle equipped with an overhead stirrer, a Dean-Stark trap and a thermocouple was charged 841.8 g of an alkenyl succinimide dispersant (derived from 2100 Mn PIB) from Afton Chemical Corporation) and 46.8 g of methyl 3-((3,5-di-t-butyl)-4-hydroxyl phenyl) propionate. The reaction mixture obtained was heated with stirring under nitrogen atmosphere at 160° C. for 4 hours. The reaction mixture was diluted with 27.8 g of process oil to afford the 854 g of product.

Evaluation of the reaction product was conducted using a Sequence VG test, which is an industry dispersant sludge test to determine the average engine sludge (AES). The Sequence VG engine sludge and varnish deposit test is a fired engine-dynamometer test that evaluates the ability of a lubricant to minimize the formation of sludge and varnish deposits. The test is a replacement for the Sequence VE test (ASTM D 5302). The test method was a cyclic test, with a total running duration of 216 hours, consisting of 54 cycles of 4 hours each. The test engine was a Ford 4.6 L, spark ignition, four stroke, eight cylinder "V" configuration engine. Features of this engine include dual overhead camshafts, a cross-flow fast burn cylinder head design, two valves per cylinder, and electronic port fuel injection. A 90-minute break-in schedule was conducted prior to each test, since a new engine build is used for each test. Upon test completion, the engine was disassembled and rated for sludge. Average engine sludge was calculated for each sample.

The reaction product of Example 3 was blended into a SAE-W-30, GF4 prototype formulation. The formulation contained other additives such as detergent(s), antioxidant(s), antiwear agent(s), metal dithiophosphate(s), friction modifier(s), viscosity index improver(s), pour point depressant(s) and base oil(s). For comparative Example 1, a succinimde type dispersant (HiTEC® 1932 brand dispersant from Afton Chemical Corporation), which was used as a starting material in this Example, was blended into a separate SAE-W-30, GF-4 prototype formulation. For Comparative Example 2, another succinimide type dispersant (HiTEC® 1921 brand dispersant from Afton Chemical Corporation) was capped with a phenolic-free hydroxy carboxylic acid and was blended into a separate SAE-W-30, GF-4 prototype formulation.

| Sequence VG Engine Test Results | |
|---|---|
| Dispersant | AES Rating |
| Example 3 | 9.33 |
| Comp. Ex. 1 | 8.07 |
| Comp. Ex. 2 | 7.20 |

According to the foregoing example, using the reaction product (dispersant) according to the invention provided an AES rating that was significantly higher than the rating obtained with a commercially available dispersant (HiTEC® 1932 dispersant), and was even more significantly higher than the rating obtained with another commercially available dispersant used in Comparative Example 2. The higher the AES rating the better is the sludge handling capability of the lubricant. A rating above 7.8 is a pass rating for the Sequence VG engine test.

At numerous places throughout this specification, reference has been made to a number of U.S. patents. All such cited documents are expressly incorporated in full into this disclosure as if fully set forth herein.

The foregoing embodiments are susceptible to considerable variation in its practice. Accordingly, the embodiments are not intended to be limited to the specific exemplifications set forth hereinabove. Rather, the foregoing embodiments are within the spirit and scope of the appended claims, including the equivalents thereof available as a matter of law.

The patentee does not intend to dedicate any disclosed embodiments to the public, and to the extent any disclosed modifications or alterations may not literally fall within the scope of the claims, they are considered to be part hereof under the doctrine of equivalents.

What is claimed is:

1. A dispersant reaction product having an antioxidant moiety, at least one polar structural domain, and at least one hydrocarbyl structural domain, is obtained under conditions effective to react reactants that consist essentially of a hindered phenolic antioxidant ester and a reactable dispersant, said reactable dispersant comprising a Mannich dispersant.

2. A dispersant reaction product according to claim 1, wherein said hindered phenolic antioxidant ester is represented by the structure:

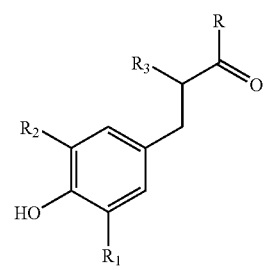

wherein R is an alkoxy, $R_1$ and $R_2$ independently represent a linear or branched alxyl group of 1 to 6 carbon atoms, and $R_3$ represents a lower alkyl group or a hydrogen atom.

3. A dispersant reaction product according to claim 2, wherein R represents —$OC_{1-6}$.

4. A dispersant reaction product according to claim 2, wherein $R_1$ is on alkyl group of 1 to 6 carbon atoms.

5. A dispersant reaction product according to claim 2, wherein $R_2$ represents an alkyl group of 1 to 6 carbon atoms.

6. A dispersant reaction product according to claim 2, wherein at least one of $R_1$ and $R_2$ represents a tert-butyl group.

7. A dispersant reaction product according to claim 3, wherein R represents —$OCH_3$.

8. A dispersant reaction product according to claim 3, wherein $R_3$ represents a methyl group of hydrogen.

9. A dispersant reaction product according to claim 1, wherein the conditions include using a radio of molar equivalents of hindered phenolic compound to reactable dispersant of 0.01 n to n, wherein n represents the number of nitrogen atoms in said reactable dispersant.

10. A lubricating composition comprising
a major amount of base oil; and
a minor amount of a dispersant reaction product according to claim 1.

11. An internal combustion engine lubricated with a lubricating composition according to claim 10.

12. A method for lowering soot and sludge deposits in an internal combustion engine comprising lubricating an internal combustion engine with a lubricating composition according to claim 10.

13. A method for improving dispersion of soot in a diesel engine comprising lubricating said diesel engine with a composition according to claim 10.

14. A formulated additive package comprising a dispersant according to claim 1, optionally at least one other additive suitable for an oil-based lubricating composition, and a minor amount of an oil.

15. A formulated additive package according to claim 14, wherein said additive package comprises 10 wt. % to 80 wt. % of said dispersant.

16. A dispersant reaction product having an antioxidant moiety, at least one polar structural domain, and at least one hydrocarbyl structural domain, obtained under conditions effective to react reactants that consist essentially of a hindered phenolic antioxidant ester and a reactable dispersant, said reactable dispersant comprising a succinimide-based dispersant or a Mannich-based dispersant, said hindered phenolic antioxidant ester being represented by the structure:

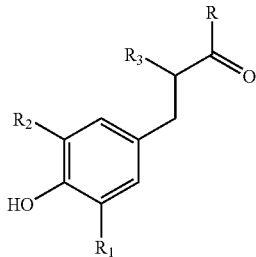

wherein R is an alkoxy, $R_1$ and $R_2$ independently represent a linear branched alxyl group having 1 to 6 carbon atoms, and $R_3$ represents a lower alkyl group or a hydrogen atom, the reactable dispersant consisting essentially of a succinimide-based dispersant having at least one alkyl chain, and the dispersant reaction product is represented by the structure:

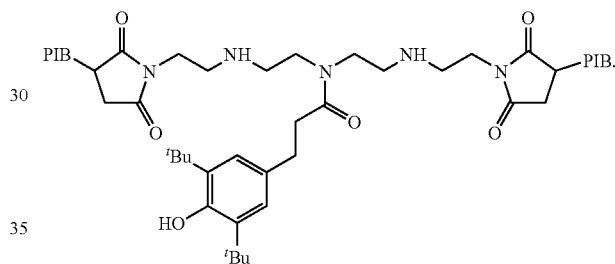

* * * * *